(12) United States Patent
Toffano et al.

(10) Patent No.: US 6,620,792 B1
(45) Date of Patent: Sep. 16, 2003

(54) PHARMACEUTICAL COMPOSITIONS CONTAINING MONOSIALOGANGLIOSIDE $GM_1$ OR DERIVATIVE THEREOF SUITABLE FOR THE TREATMENT OF PARKINSON'S DISEASE

(75) Inventors: Gino Toffano, Padova (IT); Aurelio Romeo, Rome (IT); Stephen Drake Skaper, Vicenza (IT)

(73) Assignee: Fidia S.p.A., Abano Terme (IT)

(*) Notice: Subject to any disclaimer, the term of this patent is extended or adjusted under 35 U.S.C. 154(b) by 0 days.

(21) Appl. No.: 08/304,391

(22) Filed: Sep. 12, 1994

Related U.S. Application Data

(63) Continuation-in-part of application No. PCT/EP93/00571, filed on Mar. 12, 1993.

(30) Foreign Application Priority Data

Mar. 13, 1992 (IT) .......................................... MI92A0591

(51) Int. Cl.⁷ ............................................. A61K 31/715
(52) U.S. Cl. ............................. 514/25; 514/54; 514/61
(58) Field of Search ............................... 514/25, 54, 61

(56) References Cited

U.S. PATENT DOCUMENTS

| 4,713,374 A | * | 12/1987 | della Valle et al. ........... 514/54 |
| 5,229,373 A | * | 7/1993 | della Valle ................... 514/61 |

FOREIGN PATENT DOCUMENTS

| EP | 0167449 | | 1/1986 |
| EP | 0373039 | * | 6/1990 |
| WO | 93/03049 | * | 2/1983 |

OTHER PUBLICATIONS

Seren et al. *Stroke* 1990, 21(11), 1607–1612.*
Bianchi et al. *Diabet. Res. Clin. Prac.* 1991, 12, 107–111.*
Skaper et al. *Neurosci. Lett.* 1990, 117, 154–159.*
Olney et al. *Exp. Neurol.* 108, 269–272.*
Favaraon et al. *Proc. Natl. Sci. USA* Oct. 1988, 85, 7351–7355.*
N.E.J. Med., "Uneven Pattern of Dopamine Loss in the Striatum of Patients with Idiopathic Parkinson'Disease", pp. 876–880, Apr. 7, 1988.
Amer. Neurol., "Rate of Cell Death in Parkinsonism Indicates Active Neuropathological Process", vol. 24, pp. 574–576, 1988.
N.E.J. Med., "Effect of Deprenyl on the Progression of Disability in Early Parkinson's Disease", vol. 321, No. 20, pp. 1364–1371, Nov. 16, 1989.
Experimental Neurology, "Excitotoxicity of L–DOPA and 6–OH–DOPA: Implications for Parkinson's and Huntington's Diseases", vol. 108, pp. 269–272, 1990.
Proc. Nat'l. Acad Sci., "2,4,5–Trihydroxyphenylalanine in Solution Forms a Non–N–Methyl–D–Aspartate Glutamatergic Agonist and Neurotoxin", vol. 88, pp; 4865–4869, Jun. 1991.
Tins, "MPTP and Parkinson's Disease", pp. 79–83, Feb. 1985.
Neurochemistry International, "Gangliosides in the Nervous System", vol. 5, No. 5, pp. 507–537, 1983.
Stroke, "GMI Ganglioside Therapy in Acute Ischemic Stroke", vol. 20, No. 9, pp. 1143–1149.
N.E.J. Med., "Recovery of Motor Function After Spinal–Cord Injury—A Randomized Placebo–Controlled Trial With GM–1 Ganglioside", vol. 324, No. 26, pp. 1829–1837, Jun. 27, 1991.
Stroke, "Influence of Monosialoganglioside Inner Ester on Neurologic Recovery After Global Cerebral Ischemia in Monkeys", vol. 20, No. 5, pp. 652–656, May 1989.
Clinical Trials J., "Disposition of Exogenous Tritium–Labelled $GM_1$ Monosialoganglioside in the Rat", vol. 26, No. 1, pp. 39–48, 1989.
Brain, "Cognitive and Motor Deficits in the Acquisition of an Object Retrieval/Detour Task in MPTP–Treated Monkeys", (1990), 113, 617–637.
J. Immun. Methods, 65 (1983) 55–63, "Rapid Colorimetric Assay for Cellular Growth and Survival: Application to Proliferation and Cytotoxicity Assays".
Abstract, Italian Patent Application No. PD 91 000234.
Annals NY Acad. of Med., Part VII, pp. 637–676, "Developmental Time Course in Human Infants and Infant Monkeys, and The Neural Bases of, Inhibitory Control in Reaching".
Brain Res., 534 (1990), 25–36, "Chronic Exposure to Low Doses of MPTP. II. Neurochemical and Pathological Consequences in Cognitively–Impaired, Motor Asymptomatic Monkeys".
J. of Neuroscience (1988), 8(3); 733–745, "Development and Survival of Neurons in Dissociated Fetal Mesencephalic Serum Free Cell Cultures: I. Effects of Cell Density and of Adult Mammalian Striatal–Derived Neuronotrophic Fact (SDNF)".

(List continued on next page.)

*Primary Examiner*—Kathleen K. Fonda
(74) *Attorney, Agent, or Firm*—Hedman & Costigan, P.C.

(57) ABSTRACT

The present invention refers to pharmaceutical compositions containing monosialoganglioside $GM_1$ or a derivative thereof, namely, the inner ester $AGF_2$ and the methyl ester AGF4, suitable for the treatment of Parkinson's disease. A further object of the present invention is a therapy for Parkinson's disease based on the associated administration of the aforesaid compounds and, in addition, the N-dichloroacetyl lyso $GM_1$ (LIGA 20) with known pharmaceuticals active in the aforesaid treatment, in particular with L-dopa and/or BDNF.

6 Claims, 4 Drawing Sheets

OTHER PUBLICATIONS

Figure 1A:
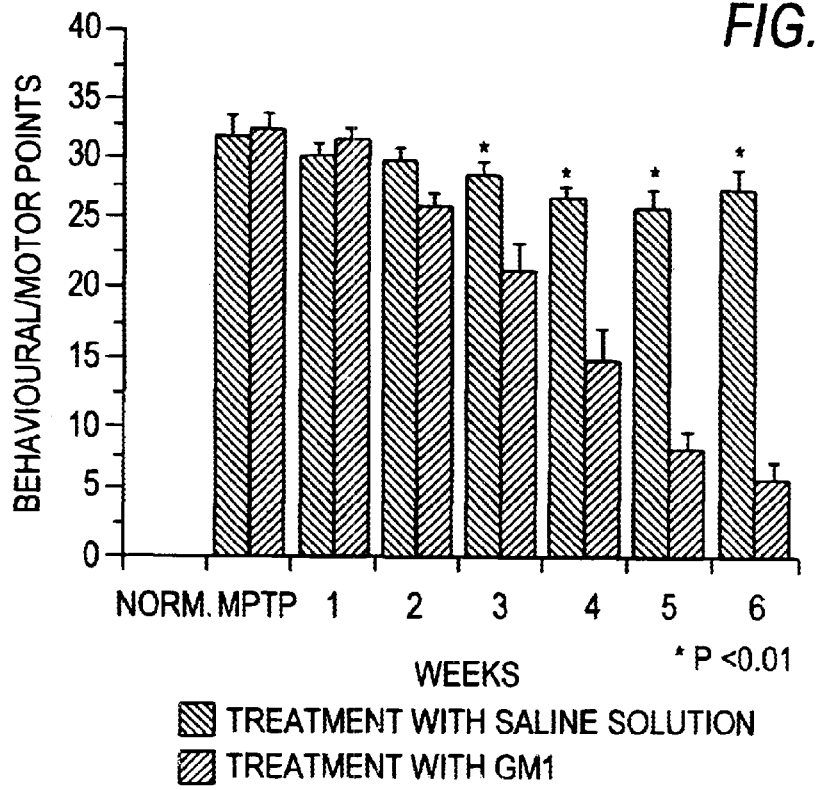
Figure 1B:
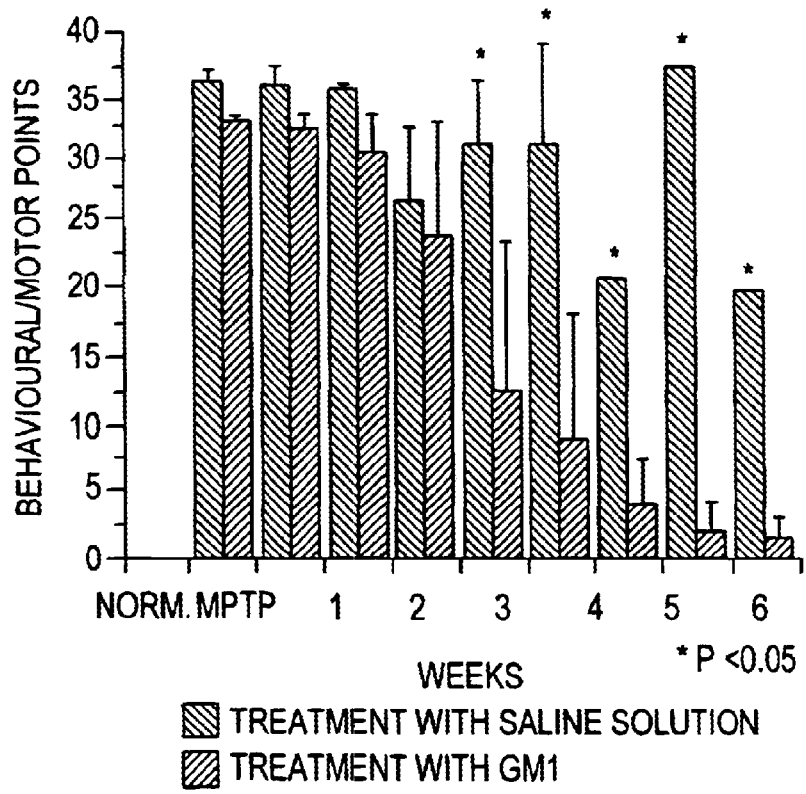
Figure 1C:
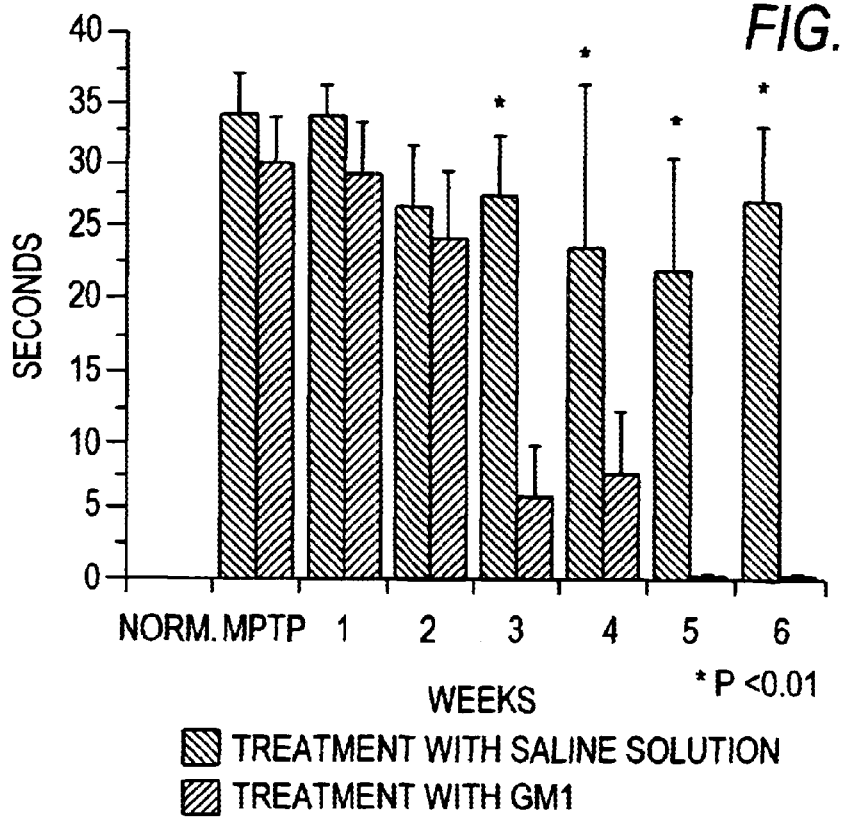
Figure 1D:
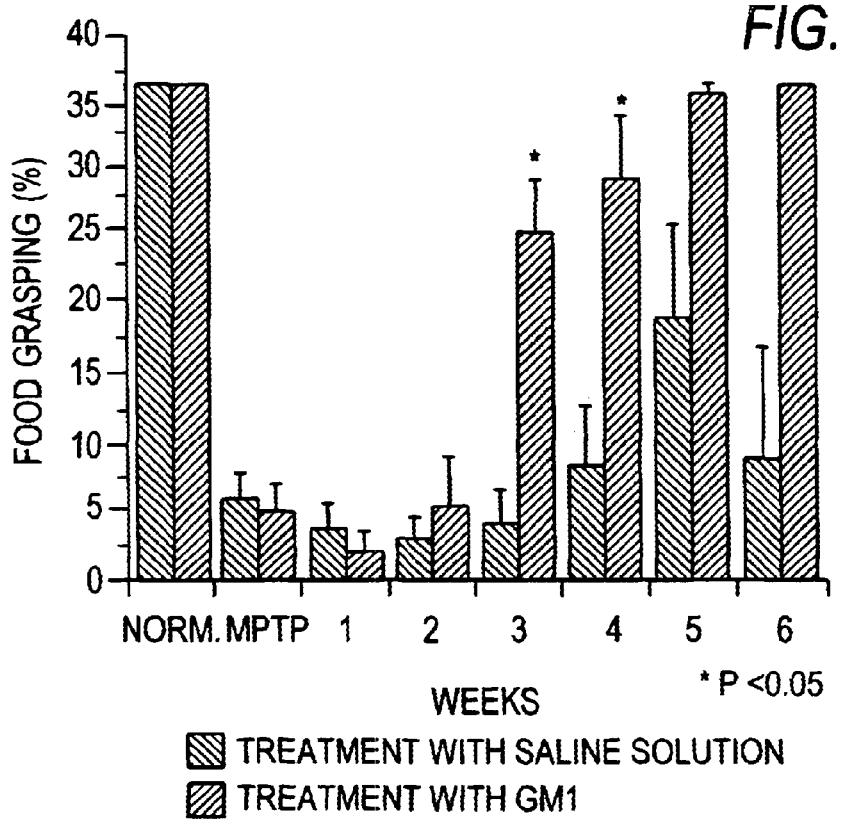

Methods in Neurosciences, vol. 2, (1990) pp. 17–33; "Culture and use of Primary Clonal Neural Cells".

Neuroscience, vol. 7, No. 1, pp. 193–205 (1982), "Long-Term Development of Mesencephalic Dopaminergic Neurons of Mouse Embryos in Dissociated Primary Cultures: Morphological and Histochemical Characteristics".

CA"Characterization of 2, 4, 5 trinydroxphenylalanine neurotoxcity in vitro and protective effects of ganglioside GM1: Implications for Parkinson's Disease", by S.D. Skaper, Journal of Pharamceutical Experimental Therapy, vol. 263, No. 3, Dec. 1992, pp. 1440–1446.

CB"MPTP–induced parkinsonism: acceleration of biochemical and behavorial recovery by GM1 ganglioside treatment", by J.S. Schenider, Journal of Neuroscience Res., Jan. 1992, 31(1), p. 112–9. Abstract Only.

CC"Further Studies on the effects of the GM1 ganglioside on the degenerative and regenerative features of mesostriated dopamine neurons", by L. F. Agnati, Acta Physiol. Scand. Suppl., 1984, 532 p. 37–44. Abstract Only.

* cited by examiner

PHARMACEUTICAL COMPOSITIONS CONTAINING MONOSIALOGANGLIOSIDE $GM_1$ OR DERIVATIVE THEREOF SUITABLE FOR THE TREATMENT OF PARKINSON'S DISEASE

This is a continuation-in-part of PCT/EP93/00571, filed Mar. 12, 1993.

TECHNICAL FIELD

This invention relates to pharmaceutical compositions containing onosialoganglioside $GM_1$ or a derivative thereof suitable for the treatment of Parkinson's disease.

PRIOR ART

Parkinson's disease is a neurodegenerative disease, which has a high rate of incidence (20 persons in 100,000 in the U.S.A.) and generally affects people older than 45-years.

Parkinson's disease is characterized by a dopaminergic deficit, which brings about a series of neuronal events resulting in akinesia, muscle rigidity, and tremors.

Symptomatology is believed to manifest itself with the loss of at least 85% of the striatal dopaminergic innervation, consequent to the degeneration of the neurons producing DA (dopamine) in the substantia nigra and pars compacta (Kish S. J. et al., The New England J. of Med:, 318, 876, 1988).

It is to be stressed that although pharmacological therapy for Parkinson's disease has been studied for over 25 years, the disease is still a critical problem especially due to the slow and progressive degeneration of the dopaminergic system (McGeer P. L. et al., Ann. Neurol., 24, 574, 1988).

As known, the therapy based on L-dopa, associated with peripheral decarboxylase inhibitors (carbidopa or benserazide), with monamine oxidase inhibitors (Shoulson I. et al.: "Effect of Deprenyl on the progression of disability in early Parkinson's disease", The New England J. of Med., 16, 1364–1371, 1989), as well as the therapy based on long-acting direct dopaminergic agonists (pergolide, cabergoline), in the great majority of early-stage cases considerably improves the clinical picture and, in some cases, provides a total control of symptoms. However, after some years treatment, i.e. from 2–3 years min. to generally 10 years max. or even more, symptoms—mainly characterized clinically by fluctuation and dyskinesias of various types—appear anew in most patients (80–90%).

Said motor fluctuations (in particular on-off phenomena) and hyperkinesias deeply upset the patient who, after years of well-being resulting from the disease being compensated by the therapy, relapses into a decompensated condition that prevents him/her from enjoying an adequate family, social, and work life.

With a view to solving the main problem to be faced by Parkinson's disease therapy, i.e. the decompensated phase, present clinical practice uses slow-release compositions based on levodopa associated with benserazide or carbidopa, long-acting direct dopaminergic agonists (pergolide, cabergoline), as well as infusion methods (lisuride and apomorphine subcutaneous infusion). However, no therapy has so far proved to be effective in slowing down or stopping the progression of the disorder, which is at the base of all complications occurring in the advanced phase of the disease.

As known, L-dopa and its hydroxylated metabolite (TOPA) may produce neurotoxic effects and worsen the disabling neurodegenerative pathology progression (Only J. W. et al.: "Excitotoxicity of L-dopa and 6-OH-dopa: implications for Parkinson's and Huntington's diseases", Exp. Neurol., 108, 268–272, 1990; Rosenberg P. A. et al.: "2,4,5-Trihydroxyphenylalanine in solution forms a non-N-methyl-D-aspartate glutamatergic agonist and neurotoxin", Proc. Natl. Acad. Sci. USA, 88, 4865–4869, 1991; Newcomer T. A. et al.: "Detection of TOPA (6-OH-DOPA) and TOPA quinone by HPLC reveals a spontaneous DOPA to TOPA conversion in aqueous solutions". Excitatory Amino Acids: Excito-toxicity I p. 83).

With a view to developing new pharmacological treatments capable of modifying the evolution of Parkinson's disease, by slowing down or inhibiting the progression of same, several experimental investigations on animals were carried out, especially aimed at identifying the neurobiological mechanisms that in parkinsonism cause cell death, in particular the death of substantia nigral cells.

Of great importance is the information obtained by using methylphenyltetrahydropyridine (MPTP), a toxic substance capable of producing a neuropathologic and neuropharmacological picture very similar to that of Parkinson's disease (Langston J. W.: "MPTP and Parkinson's disease", Trends in Neurosciences, 8, 2, 79–83, 1985). MPTP neurotoxicity was attributed to its oxidation, catalysed by monamine oxidase B, to the ionic species $MPP^+$, which is actively taken up by dopaminergic cell terminals and has a inhibitory effect on the mitochondrial oxidation of NADH-dependent substrates. This results in a loss of the substantia nigra and pars compacta dopaminergic neurons as well as of the striatum-innervating dopaminergic fibres, with consequent biochemical and behavioural deficiencies.

It is also known that gangliosides, i.e. the complex sialoglycosphingolipids that are present in neuronal membranes (Ando S.: "Gangliosides in the nervous system", Neuroch. Int., 5, 507–537, 1983) improve the neurologic course in the CNS of several experimental models of acute damage. On the basis of said results, $GM_1$ was clinically applied to treat cerebral ischemic stroke (U.S. Pat. No. 4,940,694 dated Jul. 10th, 1990; Argentino C. et al.: "$GM_1$ ganglioside therapy in acute ischemic stroke", Stroke, 20, 1143–1149, 1989) and traumatic spinal cord injury (patent application PD 91 000234 dated Dec. 23rd, 1991; Geisler F. H.: "Recovery of motor function after spinal-cord injury—a randomized placebo-controlled trial with $GM_1$ ganglioside", The New England J. of Med., 324, 1829–1838, 1991).

The inner ester derivative of $GM_1$ (AGF2) and the low-dose and fast-acting therapeutic efficacy of same, especially in acute ischemia models, is also known (Cahn R. et al.: "Influence of monosialoganglioside inner ester on neurologic recovery after global cerebral ischemia in monkeys", Stroke 20, 652–656, 1989).

Furthermore, the pharmacokinetic advantages offered by $GM_1$ ester derivatives over their precursor, $GM_1$, have already been described (Bellato P. et al.: "Disposition of exogenous tritium labelled $GM_1$ lactone in the rat", Neurochem., pp. 1–6, 1991; EP patent 85401291.1).

SUMMARY

It has surprisingly been found that the compounds selected out of the group consisting of monosialoganglioside ($GM_1$), its inner ester derivative (AGF2), its methyl ester (AGF4) and N-dicholoroacetyl lyso $GM_1$ can be successfully applied to chronic Parkinson's disease treatment for preventing or reversing the neuronal degeneration induced by a long-term L-DOPA treatment.

In fact said compounds produce a neutralizing effect on the neurotoxicity of L-Dopa metabolites such as TOPA.

Therefore, the present invention is referred to the use of the claimed compounds for the preparation of pharmaceutical compositions active in Parkinson's disease treatment and to the relevant therapeutic method.

DETAILED DESCRIPTION OF THE INVENTION

Characteristics and advantages of the therapeutic treatment of Parkinson's disease with monosialoganglioside $GM_1$, its inner ester derivative AGF2, and its methyl ester AGF4 will be illustrated in more detail in the following description referred to tests carried out on monkeys and in vitro.

The aforesaid experimental tests showed that the compounds as per the invention may be successfully used in Parkinson's disease treatment. It was also found that said compounds, and in addition the N-dichloroacetyl lyso $GM_1$ (LIGA 20) may be profitably associated with other pharmaceuticals used for the same purpose, such as L-dopa and BDNF (brain-derived neurotrophic factor).

In particular, the experiments reported below showed that:

monkeys affected by serious parkinsonian symptomatology induced by MPTP (1-methyl-4-phenyl-1,2,3,6-tetrahydropyridine) administration, after treatment with $GM_1$ and its derivatives AGF2 and AGF4 significantly recovered from the motor symptoms characteristic of Parkinson's disease (almost complete reversion of akinesia and muscle rigidity) and at the same time from cognitive deficit.

$GM_1$ and its derivatives AGF2, AGF4 and LIGA 20 prevented the neurotoxicity induced by TOPA (L-dopa oxidation product) in cultures of dopaminergic mesencephalic neurons and of cerebellar neurons.

In vivo experiments with $GM_1$ were carried out on 15 (male or female) squirrel monkeys and 4 cynomolgus monkeys.

The monkeys were administered MPTP saline solution after being anaesthesized i.m. with ketamine HCl 5 mg/kg, as follows:

0.35 mg/kg/dose, i.v. (cynomolgus monkeys)

2 mg/kg/dose, i.m. (squirrel monkeys).

MPTP was administered every third day until complete manifestation of parkinsonian motor symptomatology was obtained, i.e. akinesia, lack of responsiveness to stimulation, inability to climb, to feed autonomously, and to groom. Thirty points min. (as will be defined in the explanation of FIG. 1) had to be obtained during the 48–60 hours following the last MPTP administration; then animals in pairs were subdivided at random into two treatment groups, i.e. treatment with $GM_1$ or with saline solution.

The number of MPTP administrations and the initial symptomatology rating were the same for both groups.

$GM_1$ was chronically administered i.m. at the following dosage levels:

15 mg/kg/day to cynomolgus monkeys;

30 mg/kg/day to squirrel monkeys.

Controls were treated with saline solution.

During the first weeks of experimentation the animals were also subjected to an intensive food therapy.

The recording of the monkeys' neurologic and behavioural functions began 1–2 weeks before the start of investigation and continued for the whole duration of same.

In particular, the following functions were recorded: overall activity, ability to climb, locomotion/gait, upper and lower limb movements, detailed motor ability, bradykinesia/akinesia, dyskinesia/dystonia, carriage, tremor, balance, grooming ability, sudden immobility during movements, and ability to feed.

Tests on cynomolgus monkeys also concerned face expression changes and defence reactions.

Tests on squirrel monkeys, which concerned simple motor functions (e.g. capability of grasping food placed in deep containers), were intended to determine the response time and evaluate limb functional use. In particular, monkeys were trained to grasp raisins from a Plexiglas platform accommodating 9.5 mm dia. wells. The time taken to start grasping and the number of raisins grasped in a 6-minute time limit were recorded. All the aforesaid tests were carried out before the first meal of the day.

The behaviour and neurologic functions of cynomolgus monkeys were also tested. Said monkeys were also trained to grasp an object, which has proven to be indicative of the motor and cognitive functions of MPTP-treated monkeys (Taylor J. R. et al., Brain, 113, 617, 1990).

The grasping test was carried out according to Diamond A.: "The development and neural bases of higher cognitive functions", Annals of the New York Academy of Sciences, vol. 608, A. Diamond Ed. (The New York Academy of Sciences, New York, 637–676, 1990).

Briefly, monkeys were trained to stretch their arm out of their cage to grasp food (raisins or apple) from a Plexiglas box (15 cm×15 cm×5 cm), open on one side and fastened to a platform allowing side movement and rotation.

The box open side could happen to be in front of, on the left or on the right side of the monkey. Each experiment consisted of 30 tests. The following events were recorded: successful arm stretchings (food grasped at the first attempt), correct stretchings (food grasped after various attempts), and "barrier" stretchings (i.e. towards the closed side of the box rather than-around the box until reaching the open side of same). Should no food be grasped within 5 minutes, the test was judged to be without response.

Post-mortem neurochemical examinations of striatal tissue were carried out for the determination of dopamine (DA) and relevant metabolites, e.g. homovanillic acid (HVA), and 3,4-dihydrophenylacetic acid (DOPAC). DA and relevant metabolites striatal levels were quantified by electrochemical detention high pressure liquid chromatography (HPLC) (Schneider J. S., Brain Res., 24, 534, 1990).

Furthermore, pilot tests were carried out with a view to evaluating the motor behaviour of MPTP-treated squirrel monkeys (n=6) after i.m. administration of 20 mg/kg/day AGF2 and AGF4 for 6 weeks (experimental conditions and motor parameter evaluations identical with those mentioned above).

The results of behavioural and neurologic tests and of neuroimmunohistochemical examinations are reported below.

Figure 2A:
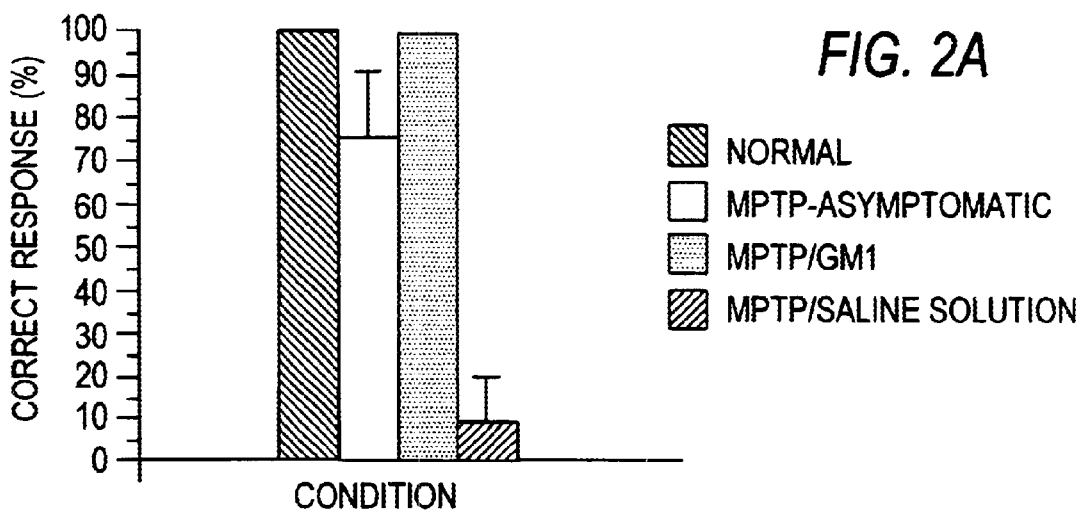
Figure 2B:
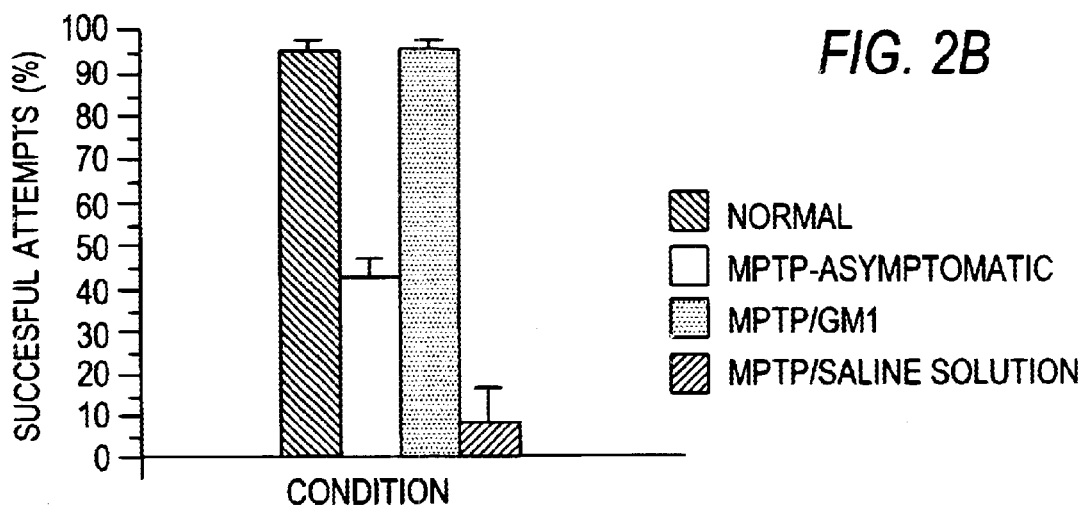
Figure 2C:
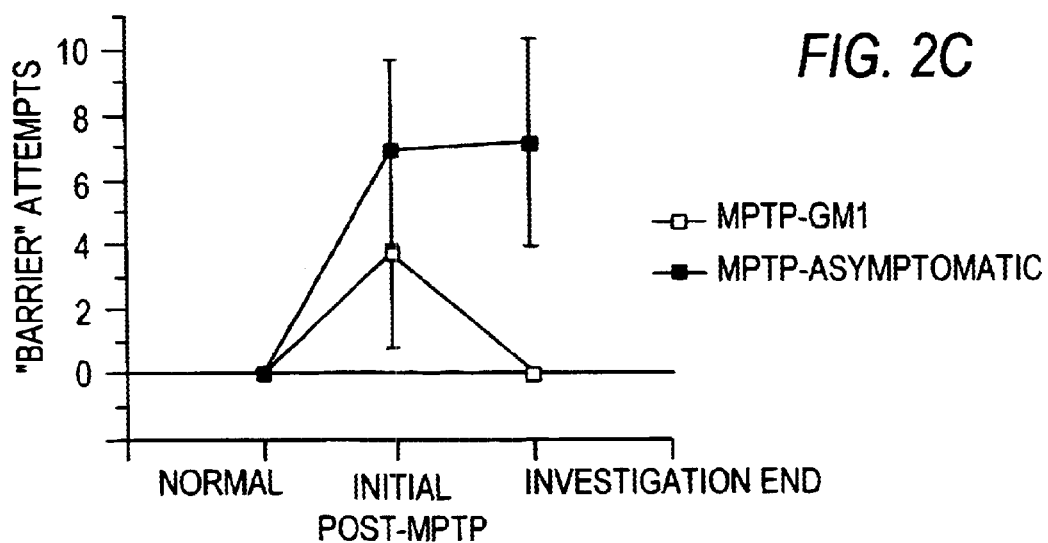

The behavioural-neurologic tests showed that:

MPTP administration causes serious Parkinson's symptomatology: altered motor behaviour (FIG. 1) and marked cognitive deficit (FIG. 2);

at the end of 6–8 weeks' investigation, $GM_1$ chronic administration can revert the parkinsonian symptomatology to an almost totally recovered (86–89%) motor behaviour. $GM_1$ efficacy is already apparent after 3–4 weeks' treatment (FIG. 1). Analogous results were obtained from tests on squirrel monkeys after AGF2 and AGF4 administration (motor behaviour average points at the 6th week: saline solution=40 (n=2); AGF2=7 (n=2); AGF4=9 (n=2).

$GM_1$ is also active in the recovery of motor-cognitive deficiencies (determined by the "object grasping" test—FIG. 2).

FIGS. 1 and 2 are now being considered in detail. FIG. 1 shows the effects produced by MPTP and $GM_1$ on motor behaviour. The behavioural/motor points referred to squirrel monkeys (A) and cynomolgus monkeys (B) are reported on the ordinate. Columns represent the average points (±S.D.); normal point is 0, MPTP points are the points recorded after the last MPTP injection but prior to the administration of associated $GM_1$-saline solution. Within the first 3–4 weeks of treatment, the monkeys treated with $GM_1$—compared with those treated with saline solution—started showing improved motor functions. At the investigation end, the monkeys treated with $GM_1$ showed an almost normal behaviour, while those treated with saline solution showed a serious parkinsonian symptomatology (*$p<0.01$ (A); *$p<0.05$ (B), Mann-Whitney test).

FIG. 1/C shows squirrel monkeys' response start time in a food grasping test. Normal monkeys started response on sighting the food container. At the initial post-MPTP condition, all monkeys had a long delay in the response start time; however, within the third week of treatment the monkeys treated with $GM_1$ started response before those treated with saline solution (*$p<0.005$). At the investigation end, the former started response almost immediately, whereas the latter were still akinetic and bradykinetic (*$p<0.002$).

FIG. 1/D shows the food per cent amount grasped during the test. Normal squirrel monkeys succeeded in grasping 100% food. Soon after MPTP administration, all monkeys were endangered and grasped approx. 15% food. Within the third week of treatment, the monkeys treated with $GM_1$—compared with those treated with saline solution—grasped a higher amount of food. At the investigation end, the former grasped 100% food whereas the latter grasped only 25% food (*$p<0.05$).

FIG. 2 illustrates the effects produced by MPTP and $GM_1$ on cynomolgus monkeys in the "object grasping" test.

FIG. 2/A shows the percentage of correct responses (the object is eventually grasped by the monkey) and FIG. 2/B the percentage of successful attempts (food is grasped at the first attempt). After some training, normal monkeys fulfilled this task almost perfectly.

In an experimental chronic treatment at low MPTP doses that did not cause any serious motor damage, monkeys found it very hard to fulfill this task.

Conversely, at the investigation end, parkinsonian monkeys treated with $GM_1$ fulfilled the task almost perfectly, whereas parkinsonian monkeys treated with saline solution found it very hard to fulfill the task, mainly due to serious motor impediment.

FIG. 2/C illustrates "barrier" attempts (towards the box closed sides) indicating response inhibition. At the early stage of a treatment, monkeys treated with $GM_1$ made several attempts of this type (in the tests in which they actually gave a response).

Neuroimmunohistochemical tests showed that:

MPTP administration remarkably decreases DA and relevant metabolite levels in the various striatal subregions examined (Table 1);

chronic treatment with $GM_1$ significantly increases DA and relevant metabolite (HVA and DOPAC) levels (Table 1), the increase being higher in less denervated regions, such as e.g. the ventrimesal region.

TABLE 1

Effects of treatment with MPTP and $GM_1$ on dopamine (DA) and metabolite (HVA and DOPAC) striatal levels. Each value represents an average (± S.D.) in ng/mg protein

| Striatal region | MPTP/$GM_1$ | | | MPTP/saline solution | | |
| --- | --- | --- | --- | --- | --- | --- |
| | DA | HVA | DOPAC | DA | HVA | DOPAC |
| Squirrel monkeys | | | | | | |
| Dorsolateral caudatum | 8.6(1.2)* | 46.2(6.5)* | 3.3(0.9)* | 2.4(0.6) | 16.4(2.7) | 0.5(1.5) |
| Ventromedial caudatum | 37.4(4.2)* | 56.6(11.9)* | 12.7(3.6)* | 8.9(2.7) | 21.0(3.3) | 3.0(1.4) |
| Dorsolateral putamen | 4.2(0.8)* | 45.9(6.9)* | 1.3(0.2)* | 1.4(0.4) | 11.9(1.4) | 0.5(0.2) |
| Ventromedial putamen | 21.9(6.1)* | 87.5(17.3)* | 5.9(1.6)* | 3.8(0.8) | 35.7(6.5) | 1.5(0.4) |
| Cynomolgus monkeys | | | | | | |
| Dorsolateral caudatum | 4.4(0.6)* | 55.9(12.0)* | 2.7(0.3)* | 0.5(0.2) | 5.3(0.7) | 0.3(0.1) |
| Ventromedial caudatum | 12.9(2.8)* | 60.9(6.9)* | 6.6(0.7)* | 1.2(0.7) | 15.5(1.8) | 1.7(0.6) |
| Dorsolateral putamen | 3.7(0.9) | 51.9(9.4)* | 2.1(0.8)* | 0.9(0.22) | 7.4(1.7) | 0.3(0.2) |
| Ventromedial putamen | 11.2(4.1)* | 100.3(11.9)* | 7.1(3.2)* | 1.7(0.3) | 21.15(3.3) | 1.0(0.5) |

(*$p < 0.05$, Mann-Whitney test)

As described hereinafter, investigations were conducted on the protective action of $CM_1$, AGF2, AGF4 and LIGA 20 on TOPA neurotoxic effect on neuronal cultures.

As known, the therapy based on L-dopa, the natural precursor of dopamine, though providing some beneficial effects on parkinsonian symptomatology, produces negative effects in the long run; actually L-dopa and its metabolites, e.g. 6-hydroxy-dopa (TOPA) can be toxic also to neurons, thus worsening the disabling neurodegenerative progression of pathology. The tests carried out by the Applicant revealed that gangliosides are effective in preventing and/or inhibiting the neurotoxicity caused by the L-dopa hydroxylated metabolite.

Therefore, the said results are indicative of the great advantage brought about by the application of said products to Parkinson's disease treatment. Patients may thus be treated with a ganglioside+L-dopa associated therapy offering the advantage of preventing and/or inhibiting the neuronal degeneration observed in parkinsonism and especially in patients treated with dopaminergic pharmaceuticals, such as L-dopa. Tests were carried out on two neuronal cultures, i.e. of mesencephalic dopaminergic neurons and of cerebellar neurons.

Mesencephalic neuron cultures were prepared according to Dal Toso et al. (Dal Toso et al.: "Development and survival of neurons in dissociated fetal mesencephalic serum-free cell cultures: I. Effects of cell density and of an adult mammalian striatal-derived neuronotrophic factor (SDNF)", J. Neurosci., 8 (3) 733–745, 1988) from the mesencephalic tegmentum of 14.5–15 days' rat embryos.

Neurons ($0.75 \times 10^6$) were plated on a poly-L-ornithine substrate in 12-well (25 mm dia. each) clusters.

Cultures were used between the fourth and the sixth day without changing the medium.

Granular cell cultures were obtained from 8-day rat cerebella and cultured ($3 \times 10^6$ cells) on plates coated with poly-L-lysine substrate according to Skaper et al. (Skaper S. D. et al.: "Culture and use of primary and clonal neural cells", Methods in Neurosciences, Ed. by P. M. Conn, Vol. 2, pp. 17–33, Academic Press, Orlando, 1990).

Twenty-four hours later, cytosine arabinoside (10 $\mu$M) was added to inhibit non-neuronal proliferation. Cerebellar granule cells were used 10–12 days later without changing the medium.

Cells were incubated with TOPA either for 40 minutes (100 $\mu$M acute exposure) or for 24 h (10 $\mu$M prolonged exposure).

Treatment with $GM_1$, AGF2, AGF4 (100 $\mu$M) and LIGA 20 (1–30 $\mu$m) was carried out as follows:

2-hour pretreatment before acute incubation with TOPA;
cotreatment only with LIGA 20 before acute incubation with TOPA;
pretreatment with/without cotreatment before (100 $\mu$M for 2 h) and/or during (100 $\mu$M for 24 h) prolonged incubation with TOPA. TOPA cytotoxicity was determined by evaluating cellular survival, and more precisely:
TH immunofluorescence (specific for tyrosine hydroxylase) in mesencephalic dopaminergic neurons, as described by Berger et al. (Berger B. et al.: "Long-term development of mesencephalic dopaminergic neurons of mouse embryos in dissociated primary cultures: morphological and histochemical characteristics", Neurosci., 7, 193–205, 1982);
MTT colorimetric assay of cerebellar neurons, as described by Mosmann (Mosmann T.: "Rapid colorimetric assay for cellular growth and survival: application to proliferation and cytotoxicity assays", J. Immunol. Meth., 65, 55–63, 1983).

Cytotoxicity is expressed as per cent cellular survival.

The results of the two tests (in triplicate) were analysed statistically according to Duncan's test. A brief description of same is reported below:

$GM_1$ (100 $\mu$M×24 h) produces a neuroprotective effect on mesencephalic dopaminergic neurons exposed to TOPA toxic levels (10 $\mu$M×24 h coincubation).

TH immunopositive neurons remain intact when coincubated with TOPA and $GM_1$ (Table 2);

also $GM_1$ derivatives (AGF2 and AGF4) produce a protective effect on the neurotoxicity caused by TOPA (Table 2);

$GM_1$ exerts a neuroprotective action on cerebellar neurons either after acute or after prolonged exposure to TOPA (100 $\mu$M×40 minutes or 10 $\mu$M×24 h).

In particular, after prolonged incubation, $GM_1$ is even more effective if cells are subjected to an associated treatment, i.e. pre- and co-treatment (100 $\mu$M $GM_1 \times 2$ h in the absence of TOPA+100 $\mu$M $GM_1 \times 24$ h in the presence of 10 $\mu$M TOPA) (Table 3).

In addition LIGA20 is dose-dependently effective in cotreatment in protecting cerebellar granule cells against the acute toxicity of topa ($ED_{50} \approx 9$ $\mu$m). Under these conditions of cotreatment $GM_1$, up to 200 $\mu$M, is not active (FIG. 3).

Figure 3:
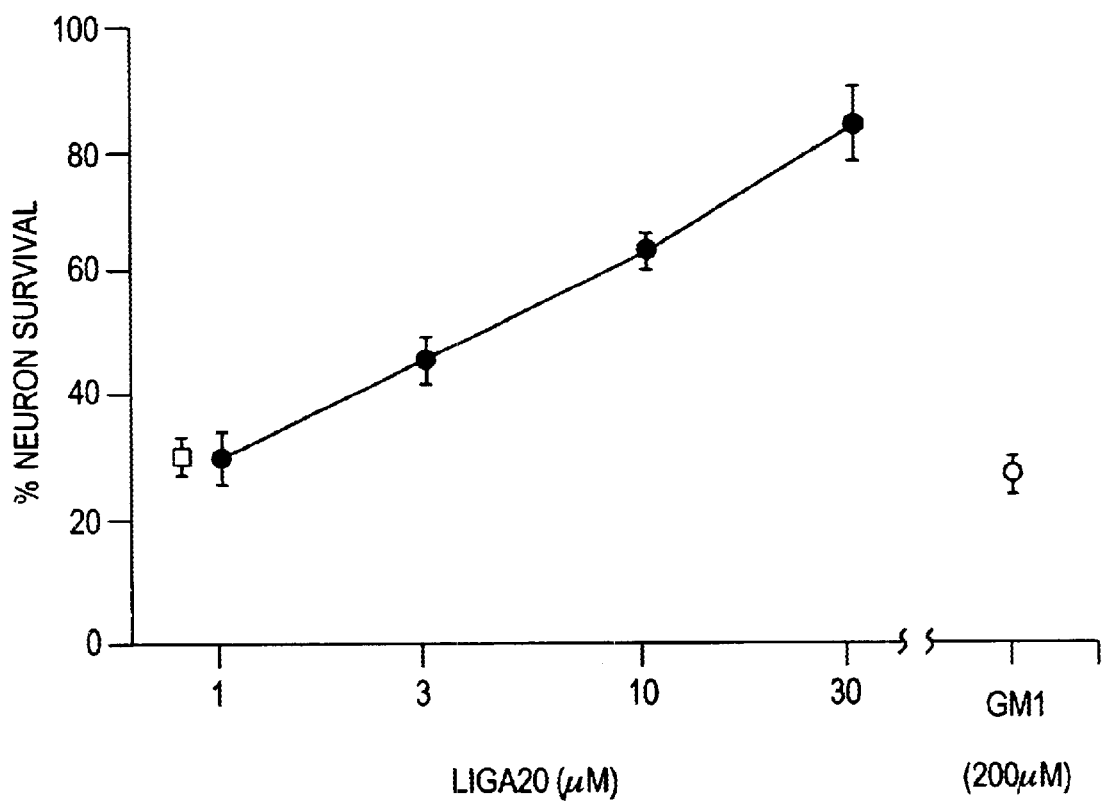

In FIG. 3 the dose-dependent protective effect of LIGA20 against TOPA-induced death of cultured cerebellar granule cells is represented. Cells were exposed concurrently to 100 $\mu$M TOPA and 1–30 $\mu$M LIGA20 or 200 $\mu$M $GM_1$ in Locke's solution for 45 minutes (24° C.), washed and returned to their original medium. Survival was assessed 24 h later by the MTT method. Means±S.E.M. (n=9, 3 experiments). TOPA ( ), LIGA 20 ( ), $GM_1$ ( ).

LIGA20 (30 $\mu$M) cotreatment produces a neuroprotective effect on mesencephalic dopaminergic neurons exposed to acute toxic levels of TOPA (100 $\mu$M×45 minutes), while $GM_1$ (200 $\mu$M) in only cotreatment is not active (Table 4).

TABLE 4

Protective effects of LIGA20 and $GM_1$ against TOPA-induced loss of dopaminergic neurons in cultures of mesencephalic cells
Cultures at 5 DIV were incubated with 30 $\mu$M LIGA20 or 200 $\mu$M $GM_1$ in Locke's solution containing 100 $\mu$M TOPA for 45 minutes (22° C.), throroughly washed and returned to their original medium. In some cases cells were treated with 200 $\mu$M $GM_1$ for 2 h (37° C.) in Locke's solution, washed, and exposed to TOPA as above. All cultures were processed for TH immunocytochemistry 24 h after termination of the exposure to TOPA, and the $TH^+$ cells were counted. Means ± S.E.M. (n = 8,4 experiments).
Control (100%) = sham-washed sister cultures without TOPA.

| Drug treatment | $TH^+$ cells (% control) |
|---|---|
| None | 5.2 ± 1.1 |
| LIGA20 | 83.9 ± 4.2 |
| $GM_1$ | 5.6 ± 0.7 |
| $GM_1$ (pretreatment) | 79.1 ± 4.0 |

$^a$p < 0.001 vs. TOPA

TABLE 2

Effect of $GM_1$ and of its derivatives (AGF2 and AGF4) on the neurotoxicity caused by TOPA to mesencephalic dopaminergic neurons

| Treatment | No. of $TH^+$ cells |
|---|---|
| Control | 244 ± 20 |
| TOPA (10 $\mu$M) | 62 ± 8 (a) |
| TOPA (10 $\mu$M) + $GM_1$ (100 $\mu$M) | 187 ± 10 (b) |
| + AGF2 (100 $\mu$M) | 225 ± 15 (c) |
| + AGF4 (100 $\mu$M) | 219 ± 11 (c) |

(a) = p < 0.02 vs control
(b) = p < 0.05 vs TOPA
(c) p < 0.05 vs $GM_1$
Mesencephalic serum-free cells were cultivated 5 days. then incubated with $GM_1$, AGF2, AGF4 (100 $\mu$M), and TOPA (10 $\mu$M) for 24 h. After fixation and immunostaining with tyrosine-hydroxylase antibodies, $TH^+$ neurons were counted. The values are an average (±S.D.) of three determinations.

TABLE 3

Effect of $GM_1$ on the neurotoxicity caused by TOPA to cerebellar granule cells

| Culture Treatment | Neuronal survival (%) |
|---|---|
| 40-minute exposure: | |
| TOPA (100 $\mu$M) | 22 ± 2.0 |
| TOPA (100 $\mu$M) + $GM_1$ | 72.4 ± 5.8 (a) |
| 24-h exposure: | |
| TOPA (10 $\mu$M) | 17.1 ± 1.4 |
| TOPA + $GM_1$ (pretreatment) | 57.0 ± 6.5 (a) |
| TOPA + $GM_1$ (pre- and co-treatment) | 75.4 ± 5.5 (b) |

In vitro granule cells at the 11th day were incubated as indicated above. In the 40-minute exposure to TOPA, $GM_1$ (100 μM) was used in 2-h pretreatment only. In the 24-minute exposure to TOPA, $GM_1$ (100 μM) was used either in 2-h pretreatment only or in 2-h pretreatment and in cotreatment with TOPA. The values are expressed with reference to the corresponding control cultures (=100%) and are an average (±S.D.) of two determinations, each being carried out in triplicate.

(a)=p<0.01 vs agonist alone
(b)=p<0.05 vs $GM_1$ pretreatment group.

The study on mesencephalic dopaminergic neurons was performed with associations of $GM_1$, $AGF_2$ and $AGF_4$ with BDNF (brain-derived neurotrophic factor) in the presence or absence of L-DOPA.

Associations of $GM_1$, $AGF_2$ and $AGF_4$ with BDNF were found to have a synergic effect in protecting mesencephalic dopaminergic neurons against TOPA-induced neurotoxicity. The effect is considerable even at extremely low concentrations of $GM_1$, $AGF_2$ and $AGF_4$ (1–10 μM) with BDNF (1 ng/ml) that is, at concentrations with no neuroprotective activity of their own. In one particular experiment, in which the mesencephalic dopaminergic neurons were placed together with 1 ng/ml of BDNF and 10 μM of $GM_1$, the number of neurons which survived the TOPA-induced toxic insult was not significantly different from that obtained using a saturation concentration (50 ng/ml) of BDNF alone.

From the results obtained the conclusion was come to that $GM_1$ and its derivatives AGF2, AGF4 and LIGA 20 protect neuronal cells against the toxicity caused by TOPA: said effect is clearly apparent not only on mesencephalic neurons (dopaminergic and not), but also on other neuronal populations, such as e.g. cerebellar neurons.

Said results are predictive of a new therapeutic application of $GM_1$ and its derivatives in parkinsonian patients treated with the traditional dopaminergic pharmaceuticals, such as L-dopa. In particular, the $GM_1$ derivative LIGA20 is more potent and faster-acting than $GM_1$ or its derivatives $AGF_2$ and $AGF_4$ and is effective when used only in cotreatment, suggesting a possible oral use of LIGA20.

The new ganglioside+L-dopa and/or BDNF associated therapy offers the great advantage of preventing and/or reversing the neuronal degeneration which is induced also by the neurotoxic effects produced by a long-term L-dopa treatment.

Therefore, monosialoganglioside $GM_1$, its inner ester derivative AGF2, and its methyl ester derivative AGF4 can be used for the preparation of pharmaceutical compositions containing a pharmacologically effective quantity of same, mixed with pharmacologically acceptable excipients and diluents, suitable for the therapeutic treatment of Parkinson's disease. Furthermore, the said compounds and the N-dichloroacetyl lyso $GM_1$ (LIGA20) may be utilized in an associated therapy with pharmaceuticals or pharmaceutical combinations to assuage the parkinsonian symptomatology and recover dopaminergic functionality.

Particularly convenient is the use of said compounds in association with L-dopa also in association with BNDF or other decarboxylase or monamine oxidase inhibitors.

The pharmaceutical compositions as per the present invention may have an active ingredient content of 10 to 200 mg per single dose, associated with one or more pharmacologically acceptable excipients or diluents and, as mentioned above, can be administered to man orally or parenterally, i.e. by intramuscolar or intravenous or subcutaneous injection.

The active ingredient dose to be administered will depend on the desired effects and on the way of administration: by parenteral injection, it may range from 0.1 to 30 mg/kg/day; by os, it may range from 0.5 to 150 mg/kg/day.

A few pharmaceuticals prepared according to this invention are reported below by way of example and not of limitation:

CASE 1
One 2 ml vial contains

| | |
|---|---|
| monosialoganglioside ($GM_1$) sodium salt | 20.00 mg |
| dibasic sodium phosphate 12 $H_2O$ | 6.00 mg |
| monobasic sodium phosphate 2 $H_2O$ | 0.50 mg |
| sodium chloride | 16.00 mg |
| water for injection | q.s. |

CASE 2
One 2 ml vial contains

| | |
|---|---|
| monosialoganglioside ($GM_1$) sodium salt | 40.00 mg |
| dibasic sodium phosphate 12 $H_2O$ | 6.00 mg |
| monobasic sodium phosphate 2 $H_2O$ | 0.50 mg |
| sodium chloride | 16.00 mg |
| water for injection | q.s. |

CASE 3
One 5 ml vial contains

| | |
|---|---|
| monosialoganglioside ($GM_1$) sodium salt | 100.00 mg |
| dibasic sodium phosphate 12 $H_2O$ | 15.00 mg |
| monobasic sodium phosphate 2 $H_2O$ | 1.25 mg |
| sodium chloride | 40.00 mg |
| water for injection | q.s. |

CASE 4
One 2 ml ampoule contains

| | |
|---|---|
| $GM_1$ methyl ester | 5.00 mg |
| sodium chloride | 16.00 mg |
| citrate buffer at pH 6 in apyrogenous distilled water | q.s. |

CASE 5
One 2 ml ampoule contains

| | |
|---|---|
| $GM_1$ methyl ester | 50.00 mg |
| sodium chloride | 16.00 mg |
| citrate buffer at pH 6 in apyrogenous distilled water | q.s. |

CASE 6
One 4 ml vial contains

| | |
|---|---|
| $GM_1$ methyl ester | 100.00 mg |
| sodium chloride | 32.00 mg |
| citrate buffer at pH 6 in apyrogenous distilled water | q.s. |

CASE 7
One 2 ml vial contains

| | |
|---|---|
| N-dichloroacetyl lyso $GM_1$ | 5.00 mg |
| sodium chloride | 16.00 mg |
| citrate buffer pH 6 in distilled water to a vol. of | 2.00 ml |

CASE 8

Pharmaceutical Compositions Prepared in Two Vials

The compositions described in this case are prepared in two vials. One vial contains the active ingredient in the form of freeze-dried powder (10% to 90% by wt.) mixed with a pharmacologically acceptable excipient, with glycine or mannitol. The other vial contains the solvent, as sodium chloride solution and a citrate buffer.

When the vial of System 6 contains the active ingredient alone, the powder may be obtained either by freeze-drying, using water for injection or another solvent (e.g. tert-butanol), or by direct partition under aseptic conditions of the sterile powder.

| System No. 1 | |
|---|---|
| a. one 2 ml freeze-dried powder vial contains | |
| monosialoganglioside (GM$_1$) inner ester | 5.00 mg |
| glycine | 30.00 mg |
| b. one 2 ml solvent ampoule contains | |
| sodium chloride | 16.00 mg |
| citrate buffer in apyrogenous distilled water | q.s. |

| System No. 2 | |
|---|---|
| a. one 3 ml freeze-dried powder vial contains | |
| monosialoganglioside (GM$_1$) inner ester | 5.00 mg |
| mannitol | 40.00 mg |
| b. one 2 ml solvent ampoule contains | |
| sodium chloride | 16.00 mg |
| citrate buffer in apyrogenous distilled water | q.s. |

| System No. 3 | |
|---|---|
| a. one 3 ml freeze-dried powder vial contains | |
| monosialoganglioside (GM$_1$) inner ester | 50.00 mg |
| mannitol | 20.00 mg |
| b. one 3 ml solvent ampoule contains | |
| sodium chloride | 24.00 mg |
| citrate buffer in apyrogenous distilled water | q.s. |

| System No. 4 | |
|---|---|
| a. one 5 ml freeze-dried powder vial contains | |
| monosialoganglioside (GM$_1$) inner ester | 100.00 mg |
| glycine | 50.00 mg |
| b. one 4 ml solvent ampoule contains | |
| sodium chloride | 32.00 mg |
| citrate buffer in apyrogenous distilled water | q.s. |

| System No. 5 | |
|---|---|
| a. one 5 ml freeze-dried powder vial contains | |
| monosialoganglioside (GM$_1$) inner ester | 100.00 mg |
| mannitol | 40.00 mg |
| b. one 4 ml solvent ampoule contains | |
| sodium chloride | 32.00 mg |
| citrate buffer in apyrogenous distilled water | q.s. |

| System No. 6 | |
|---|---|
| a. one powder vial contains: | |
| monosialoganglioside (GM$_1$) inner ester | 100.00 mg |
| b. one 4 ml solvent ampoule contains | |
| monobasic sodium phosphate 2 H$_2$O | 1.00 mg |
| dibasic sodium phosphate 12 H$_2$O | 12.00 mg |
| mannitol | 160.00 mg |
| water for injection | q.s. |

| System No. 7 | |
|---|---|
| a. one 2 ml freeze-dried powder vial contains | |
| GM$_1$ methyl ester | 5.00 mg |
| glycine | 30.00 mg |
| b. one 2 ml solvent ampoule contains | |
| sodium chloride | 16.00 mg |
| citrate buffer in apyrogenous distilled water | q.s. |

| System No. 8 | |
|---|---|
| a. one 5 ml freeze-dried powder vial contains | |
| GM$_1$ methyl ester | 150.00 mg |
| glycine | 50.00 mg |
| b. one 4 ml solvent ampoule contains | |
| sodium chloride | 32.00 mg |
| citrate buffer in apyrogenous distilled water | q.s. |

| System No. 9 | |
|---|---|
| a. one 3 ml freeze-dried powder vial contains | |
| GM$_1$ methyl ester | 50.00 mg |
| glycine | 25.00 mg |
| b. one 3 ml solvent ampoule contains | |
| sodium chloride | 24.00 mg |
| citrate buffer in apyrogenous distilled water | q.s. |

| CASE 9 One enteric coated tablet contains | mg | mg |
|---|---|---|
| monosialoganglioside (GM$_1$) inner ester | 100 | 200 |
| Excipients: | | |
| lactose | 50 | 100 |
| microcrystalline cellulose | 25 | 50 |
| sodium carboxymethylcellulose | 10 | 20 |
| polyvinylpyrrolidone | 6 | 12 |
| methacrylic acid copolymer | 10 | 20 |
| polyethylene glycol | 2 | 4 |
| magnesium stearate | 2 | 4 |
| talc | 10 | 20 |

| CASE 10 One enteric coated tablet contains | mg | mg |
|---|---|---|
| monosialoganglioside (GM$_1$) inner ester | 100 | 200 |
| Excipients: | | |
| hydroxypropyl methylcellulose | 30 | 60 |
| lactose | 103 | 206 |
| microcrystalline cellulose | 30 | 60 |
| methacrylic acid copolymer | 16 | 32 |
| polyethylene glycol | 3 | 6 |
| magnesium stearate | 3 | 6 |
| talc | 15 | 30 |

| CASE 11 One immediate release tablet contains | mg | mg |
|---|---|---|
| monosialoganglioside (GM$_1$) inner ester | 100 | 200 |
| Excipients: | | |
| lactose | 50 | 100 |
| microcrystalline cellulose | 25 | 50 |
| sodium carboxymethylcellulose | 10 | 20 |
| polyvinylpyrrolidone | 6 | 12 |
| magnesium stearate | 2 | 4 |
| talc | 5 | 10 |

| CASE 12 One controlled release tablet contains | mg | mg |
|---|---|---|
| monosialoganglioside (GM$_1$) inner ester | 100 | 200 |
| Excipients: | | |
| hydroxypropyl methylcellulose | 30 | 60 |
| lactose | 120 | 240 |

-continued

| | mg | mg |
|---|---|---|
| microcrystalline cellulose | 30 | 60 |
| magnesium stearate | 3 | 6 |
| talc | 5 | 10 |
| CASE 13 One hard gelatin capsule enclosing enteric granules contains | mg | mg |
| monosialoganglioside (GM$_1$) inner ester | 100 | 200 |
| Excipients: | | |
| saccharose | 93 | 140 |
| maize starch | 30 | 45 |
| polyvinylpyrrolidone | 25 | 37 |
| magnesium stearate | 30 | 45 |
| methacrylic acid copolymer | 25 | 37 |
| polyethylene glycol | 5 | 8 |
| talc | 10 | 15 |

What is claimed is:

1. A therapeutic method for preventing or reversing the neuronal degeneration induced by a neurotoxic effect of trihydroxylated L-dopa metabolite (TOPA) which is produced by treatment of Parkinson's disease with L-dopa therapy, said therapeutic method consisting of administering a drug selected from the group consisting of GM1, the inner ester of GM1 which is known as AGF2, or the methyl ester of GM1 which is known as AGF4 at a dosage, which is a pharmacologically effective amount, alone or in association with other drugs, to a patient in need of such treatment.

2. The therapeutic method according to claim 1, wherein said administration is associated with pharmaceuticals selected from the group consisting of L-dopa, BNDF, and combinations thereof with decarboxylase or monoaminoxidase inhibitors.

3. The therapeutic method of claim 1 wherein said administration is associated with the administration of L-dopa.

4. The therapeutic method of claim 1 wherein the drug is GM1.

5. The therapeutic method of claim 1 wherein the drug is AGF2.

6. The therapeutic method of claim 1 wherein the drug is AGF4.

* * * * *